(12) United States Patent
Shimizu et al.

(10) Patent No.: US 6,228,391 B1
(45) Date of Patent: May 8, 2001

(54) AMIDINE DERIVATIVES AND DRUG CARRIERS COMPRISING THE SAME

(75) Inventors: Kazuhiro Shimizu; Masashi Isozaki; Kazunori Koiwai, all of Kanagawa (JP)

(73) Assignee: Terumo Kabushiki Kaisha, Tokyo (JP)

( * ) Notice: Subject to any disclaimer, the term of this patent is extended or adjusted under 35 U.S.C. 154(b) by 0 days.

(21) Appl. No.: 09/202,193

(22) PCT Filed: May 1, 1997

(86) PCT No.: PCT/JP97/01494

§ 371 Date: Dec. 10, 1998

§ 102(e) Date: Dec. 10, 1998

(87) PCT Pub. No.: WO97/42166

PCT Pub. Date: Nov. 13, 1997

(30) Foreign Application Priority Data

May 2, 1996 (JP) .................................................. 8-111532

(51) Int. Cl.$^7$ ...................... C07C 257/14; C07C 335/32; C07C 335/36; A61K 47/16; A61K 9/127
(52) U.S. Cl. ..................... 424/450; 424/1.21; 424/9.321; 424/9.51; 424/94.3; 935/54; 564/225; 564/244
(58) Field of Search ..................... 424/400, 450, 424/1.21, 9.321, 9.51, 94.3; 935/54; 564/225, 244

(56) References Cited

U.S. PATENT DOCUMENTS

| | | | |
|---|---|---|---|
| 5,023,087 | * | 6/1991 | Van-Young ........................ 426/450 |
| 5,171,678 | | 12/1992 | Behr et al. . |
| 5,334,761 | | 8/1994 | Gebeyehu et al. . |
| 5,552,157 | | 9/1996 | Yagi et al. . |

FOREIGN PATENT DOCUMENTS

| | | |
|---|---|---|
| 2--76810 | 3/1990 | (JP) . |
| 2-292246 | 3/1990 | (JP) . |
| 4-5226 | 1/1992 | (JP) . |
| 4-108391 | 4/1992 | (JP) . |
| 4-108391 | 9/1992 | (JP) . |
| 6-210155 | 8/1994 | (JP) . |
| 6-3229558 | 11/1994 | (JP) . |
| 7-316079 | 12/1995 | (JP) . |
| 8-27030 | 1/1996 | (JP) . |
| 8-59503 | 3/1996 | (JP) . |

OTHER PUBLICATIONS

English abstract of JP 2–292246(A).

English abstract of JP 4–108391 (A).

* cited by examiner

*Primary Examiner*—Gollamudi S. Kishore
(74) *Attorney, Agent, or Firm*—Burns, Doane, Swecker & Mathis, LLP

(57) ABSTRACT

Novel amidine derivatives of the formula (1); and drug carriers such as liposomes or emulsions comprising the derivatives, which can enclose genetic materials or drugs and transfer them to cells or affected sites efficiently and safely,

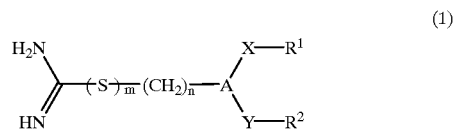

(1)

wherein A is an aromatic ring, $R^1$ and $R^2$ are the same or different and independently represent an alkyl group having any one of 10 to 25 carbon atoms, and an alkenyl group having any one of 10 to 25 carbon atoms, X and Y are the same or different and independently represent —O—, —S—, —COO—, —OCO—, —CONH—, or —NHCO—, m is 0 or 1, and n is 0 or a natural number of 1 to 6.

17 Claims, No Drawings

AMIDINE DERIVATIVES AND DRUG CARRIERS COMPRISING THE SAME

This application is a 371 of PCT/JP97/01494 filed May 1, 1997.

TECHNICAL FIELD

The present invention relates to a novel amidine derivative and a drug carrier comprising it.

BACKGROUND ART

Recently, studies have been actively made for applications of closed vesicles such as liposome, emulsion, and lipid microsphere as drug carriers have been activity made for drug delivery system (hereinafter referred to as DDS). These closed vesicles are usually prepared using phospholipids or their derivatives, sterols, or lipids except phospholipids as basic membrane-constituting materials. However, the closed vesicles composed of only these basic materials could not overcome various problems occurring in the practical use, such as mutual aggregation of closed vesicles and shortened retention time in circulation. Furthermore, it was practically difficult for them to drive drugs to their target sites.

In order to improve a drug-loading and cell binding ability of the closed vesicles, an attempt has been made to charge the surface of the closed vesicles to cationic at physiological pH range by charging a small amount of a cationic lipid such as stearylamine. In particular, cationic liposomes containing DNA are well known to promote transfer of the DNA into cells, that is, transfection, and those liposomes having higher introduction efficiency, higher expression level, and higher safety level are strongly required. But, there are limited kinds of lipid available to use for cationic liposome, then it has been desired to develop cationic lipids usable for a drug carrier that are highly safe and exhibit high performance. Such cationic lipids have been reported so far in U.S. Pat. Nos. 4,897,355, 5,334,761, JP-A 2-292246, and JP-A 4-108391. However, their effects are not satisfactory.

Therefore, it has been eagerly desired to develop a drug carrier that can transfect a DNA into cells efficiently and safely. And regarding other purpose in addition to the transfection of a DNA, the effective and safety carriers are also required for effective DDS therein to enable accurate, efficient, and safe targeting of a drug to such as injured sites in vascular endothelium and affected sites caused by nephritis, kidney cancer, pneumonia, lung cancer, hepatitis, hepatoma, pancreatic cancer, lymphoma, etc.

DISCLOSURE OF THE INVENTION

An objective of the present invention is to provide a drug carrier that enables transfection of nucleic acids, polynucleotides, genes, and their analogues into cells efficiently and safely, and to provide a cationic lipid capable of forming such drug carrier. Another objective of the present invention is to provide a drug carrier that effectively delivers a desired drug, peptide, or protein to target sites, and to provide a cationic lipid capable of forming such drug carrier.

The above objectives are achieved by the present invention as described below.

(1) An amidine derivative represented by the formula 1 or a salt thereof:

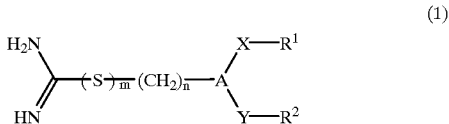

wherein A is an aromatic ring, $R^1$ and $R^2$ are the same or different and independently represent an alkyl group having any one of 10 to 25 carbon atoms, and an alkenyl group having any one of 10 to 25 carbon atoms, X and Y are the same or different and independently represent —O—, —S—, —COO—, —OCO—, —CONH—, or —NHCO—, m is 0 or 1, and n is 0 or a natural number of 1 to 6.

(2) A drug carrier comprising the amidine derivative as described in (1) as a constituent.

(3) The drug carrier as described in (2), wherein said carrier encloses a drug for diagnosis and/or therapy.

(4) The drug carrier as described in (2) or (3), wherein said carrier has an external diameter of 0.02 to 250 μm.

(5) The drug carrier as described in (2) to (4), wherein said carrier is constituted by at least one of liposomes, emulsions, macromolecules, fine aggregates, fine particles, microspheres, and nanospheres.

(6) The drug carrier as described in (2) to (5), wherein said carrier contains phospholipids or their derivatives, and/or lipids other than phospholipids or their derivatives, and/or a stabilizer, and/or an antioxidant, and/or the other surface modifier.

(7) The drug carrier as described in (2) to (6), wherein said drug for diagnosis and/or therapy is a nucleic acid, a polynucleotide, a gene, or their analogues.

(8) The drug carrier as described in (2) to (6), wherein said drug for diagnosis and/or therapy is an antiinflammatory agent, a steroid agent, an anticancer agent, an enzyme agent, an enzyme inhibitor, an antibiotic, an antioxidant, a lipid-intake inhibitor, a hormone agent, an angiotensinase inhibitor, an angiotensin receptor antagonist, an inhibitor of proliferation and migration of smooth muscle cells, a platelet-aggregation inhibitor, an inhibitor of releasing a chemical mediator, an enhancer or inhibitor of proliferation of vascular endothelial cells, an aldose reductase inhibitor, a mesangial cell-proliferation inhibitor, a lipoxygenase inhibitor, an immunosuppressant, an immunpotentiator, an antiviral agent, or a radical scavenger.

(9) The drug carrier as described in (2) to (6), wherein said drug for diagnosis and/or therapy is a glycosaminoglycan or its derivative.

(10) The drug carrier as described in (2) to (6), wherein said drug for diagnosis and/or therapy is an oligo- and/or poly-saccharide or their derivatives.

(11) The drug carrier as described in (2) to (6), wherein said drug for diagnosis and/or therapy is a protein or a peptide.

(12) The drug carrier as described in (2) to (6), wherein said drug for diagnosis and/or therapy is an endogenous diagnostic agent including an X ray contrast medium, a radioisotopically labeled nuclear medical diagnostic agent, and an agent for diagnosis by nuclear magnetic resonance.

The compounds of the present invention represented by the formula 1 are all novel. An example of their synthetic process is shown below. However, the present invention is not construed to be limited thereto.

For example, the compounds can be produced by introducing thiourea to the moiety of Z of the compound represented by the following formula 2 when Z is a halogen atom or by converting Z to an amidino group when Z is —CN.

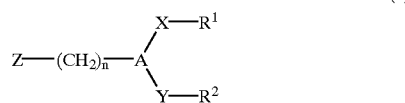

(2)

In the formula 2, A is an aromatic ring, $R^1$ and $R^2$ are the same or different and independently represent an alkyl group having 10 to 25 carbon atoms, an alkenyl group having 10 to 25 carbon atoms, X and Y are the same or different and independently represent —O—, —S—, —COO—, —OCO—, —CONH—, or —NHCO—, and n is 0 or a natural number of 1 to 6. Z is a halogen atom or —CN.

The thus-produced amidine derivatives represented by the formula 1 can be isolated and recovered by per se known separation and purification methods (for example, chromatography and recrystallization).

The carrier of the present invention preferably has a particle diameter of 0.02 to 250 µm, more preferably 0.05 to 0.4 µm.

Its structure can take various forms and does not have to be limited. The carrier is most preferably formed by at least one of macromolecules, fine aggregates, fine particles, microspheres, nanospheres, liposomes, and emulsions, which can potentially function to load drugs in a high concentration.

In the present invention, compositions of the drug carrier are not particularly limited as long as they can take the above-described forms. In view of safety, in vivo stability, the compositions preferably contain phospholipids, their derivatives, lipids other than phospholipids, their derivatives, a stabilizer, an antioxidant, and some other surface modifier.

Examples of phospholipids are natural or synthetic phospholipids including phosphatidylcholine (lecithin), phosphatidylglycerol, phosphatidic acid, phosphatidylcholine, phosphatidylethanolamine, phosphatidylserine, phosphatidylinositol, sphingomyelin, cardiolipin, and their hydrogenated products obtained by usual methods.

Examples of the stabilizers include sterols, such as cholesterol, which reduce membrane fluidity, glycerol, or saccharides such as sucrose.

The antioxidants include tocopherol homologues, namely vitamin E. There are four tocopherol isomers, $\alpha$, $\beta$, $\gamma$, and $\delta$. Any of them can be used in the present invention.

The other surface modifiers include derivatives of hydrophilic polymers and water-soluble polysaccharides such as glucuronic acid, sialic acid, and dextran.

Examples of the hydrophilic polymers include polyethylene glycol, dextran, pullulan, Ficoll, polyvinyl alcohol, styrene-maleic anhydride alternating copolymer, divinyl ether-maleic anhydride alternating copolymer, synthetic polyamino acid, amylose, amylopectin, chitosan, mannan, cyclodextrin, pectin, and carrageenan. Among them, polyethylene glycol remarkably prolongs residency in blood.

The hydrophilic Polymers can form derivatives by combining with hydrophobic compounds such as long-chain aliphatic alcohols, sterols, polyoxypropylene alkyls, and glycerol fatty acid esters. Hydrophobic compound moieties of the derivatives can be stably inserted into membranes of drug carriers (for example, liposome). Thus, hydrophilic polymers can be allowed to exist on the surface of the drug carrier. Such a hydrophilic polymer derivative that can be specifically used in the present invention is exemplified by polyethylene glycol-phosphatidylethanolamine and the like.

The drugs to be enclosed in the drug carriers can be pharmacologically active compounds, physiologically active compounds, or diagnostic substances, which are pharmaceutically acceptable, depending on the diagnostic and/or therapeutic purpose.

Basically the properties of the drug to be loaded are not limited to any particular substances, electrically neutral or anionic substances can be loaded in good efficiency because the surface of the carrier has characteristically the positive charge.

The kind of the therapeutic drug to be entrapped is not particularly limited as long as it does not affect the formation of the drug carrier. Specific examples of the drug include nucleic acids, polynucleotides, genes and their analogues, an antiinflammatory agent, a steroid agent, an anticancer agent, an enzyme agent, an enzyme inhibitor, an antibiotic, an antioxidant, a lipid-intake inhibitor, a hormone agent, an angiotensinase inhibitor, an angiotensin receptor antagonist, an inhibitor of proliferation and migration of smooth muscle cells, a platelet-aggregation inhibitor, an inhibitor of releasing a chemical mediator, an enhancer or inhibitor of proliferation of vascular endothelial cells, an aldose reductase inhibitor, a mesangial cell-proliferation inhibitor, a lipoxygenase inhibitor, an immunosuppressant, an immunopotentiator, an antiviral agent, or a radical scavenger, proteins, peptides and the like.

The kind of the diagnostic drug to be entrapped is not particularly limited as long as it does not affect the formation of the drug carrier. Specifically, such drugs includes X ray contrast mediums, radioisotopically labeled nuclear medical diagnostic agents, and agents for diagnosis by nuclear magnetic resonance.

The drug carriers of the present invention can be readily obtained by any suitable method in the art. An example thereof is described below. The amidine derivative represented by the formula 1, phospholipid, and the other components are mixed in an organic solvent such as chloroform in a flask. After the organic solvent is removed by evaporation, the residue is dried under vacuum to form a thin film on the inner wall of the flask. A drug is added to the flask and vigorously stirred to obtain a liposome suspension. The resulting liposome suspension was centrifuged and the supernatant containing the drug that has not been loaded is removed by decantation. Thus, the drug carrier suspension can be obtained. Alternatively, the drug carrier can be obtained by discharging the mixture of the above-described components under high pressure with a high-pressure discharging emulsifier.

BEST MODE FOR CARRYING OUT THE INVENTION

The following examples and test examples illustrate the present invention in more detail, but are not to be construed to limit the scope of the present invention.

(EXAMPLE 1)

Synthesis of 3,5-dipentadecyloxybenzamidine 3,5-dihydroxybenzonitrile (0.50 g), 1-bromopentadecane (2.70 g), potassium carbonate (2.56 g), and 30 ml of acetone were mixed and the mixture was heated overnight under reflux. After water was added, the mixture was extracted with methylene chloride. The extract was washed with water and dried over anhydrous magnesium sulfate. The solvent was removed by evaporation to obtain 0.33 g of 3,5-dipentadecyloxybenzonitrile as colorless crystals. This product was dissolved in a mixed solvent of 20 ml of methanol and 35 ml of benzene and hydrogen chloride gas was allowed to flow into the mixture for 1 hour under ice-cooling. The solvent was removed by evaporation under reduced pressure and the thus-obtained crystals were recrystallized from chloroform and hexane to obtain 0.28 g of 3,5-dipentadecyloxy-α-methoxy-α-iminotoluene hydrochloride. This product was dissolved in 10 ml of chloroform, ammonia gas was allowed to flow into the solution for 40 minutes under ice-cooling, then the mixture was heated for 4.5 hours under reflux. After the solvent was removed by evaporation under reduced pressure, the materials insoluble in chloroform were removed from the resulting solid to obtain 0.20 g of 3,5-dipentadecyloxybenzamidine as colorless crystals. The data obtained by instrumental analysis of this compound support the structure represented by the following formula 3.

$^1$H-nmr (CDCl$_3$) δ (ppm): 6.92 (s, 2H), 6.65 (s, 1H), 3.99 (t, 4H, J=6.4 Hz), 1.77–1.22 (m, 52H), 0.88 (t, 6H, J=6.8Hz). melting point: 149–150° C.

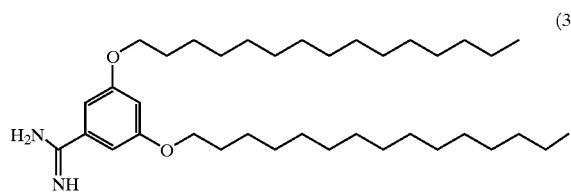

(3)

(EXAMPLE 2)

Synthesis of 3,5-dihexadecyloxybenzamidine

The method of Example 1 was repeated except for using 1-bromohexadecane in place of 1-bromopentadecane to produce a desired compound whose structure is represented by the following formula 4 and whose properties are shown below.

$^1$H-nmr (CDCl$_3$) δ (ppm): 6.93 (s, 2H), 6.64 (s, 1H), 3.98 (t, 4H, J=6.5 Hz), 1.78–1.70 (m, 4H), 1.47–1.15 (m, 52H), 0.88 (t, 6H, J=6.8 Hz). melting point: 109–110° C.

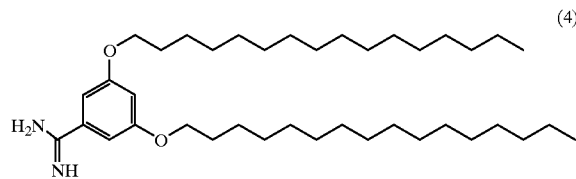

(4)

(EXAMPLE 3)

Synthesis of 3,5-dioctadecyloxybenzamidine

The method of Example 1 was repeated except for using 1-bromooctadecane in place of 1-bromopentadecane to produce a desired compound whose structure is represented by the following formula 5 and whose properties are shown below.

$^1$H-nmr (CDCl$_3$) δ (ppm): 6.91 (s, 2H), 6.65 (s, 1H), 3.99 (t, 4H, J=6.5 Hz), 1.80–1.70 (m, 4H), 1.47–1.18 (m, 60H), 0.88 (t, 6H, J=6.8 Hz). melting point: 146–148° C.

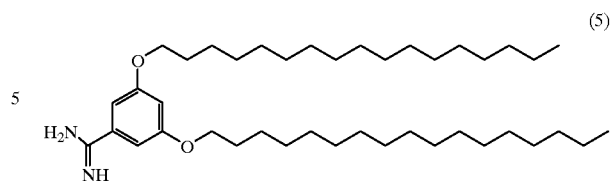

(5)

(EXAMPLE 4)

Synthesis of 3,5-didecyloxybenzamidine

The method of Example 1 was repeated except for using 1-bromodecane in place of 1-bromopentadecane to produce a desired compound whose structure is represented by the following formula 6 and whose properties are shown below.

$^1$H-nmr (CDCl$_3$) δ (ppm): 6.96 (s, 2H), 6.58 (s, 1H), 3.96 (t, 4H, J=6.5 Hz), 1.77–1.66 (m, 4H), 1.44–1.19 (m, 28H), 0.88 (t, 6H, J=6.8 Hz). melting point: 127–128° C.

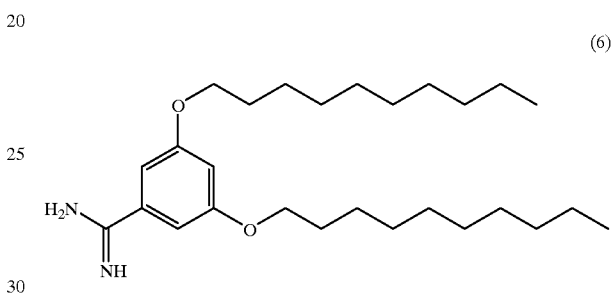

(6)

(EXAMPLE 5)

Synthesis of 3,4-didecyloxybenzamidine

The method of Example 1 was repeated except for using 3,4-dihydroxybenzonitrile in place of 3,5-dihydroxybenzonitrile and using 1-bromodecane in place of 1-bromopentadecane to produce a desired compound whose structure is represented by the following formula 7 and whose properties are shown below.

$^1$H-nmr (CDCl$_3$—CD$_3$OD) δ (ppm): 7.43–7.28 (m, 2H), 7.01–6.95 (m, 1H), 4.12–4.01 (m, 4H), 1.91–1.78 (m, 4H), 1.54–1.12 (m, 28H), 0.94–0.84 (m, 6H).

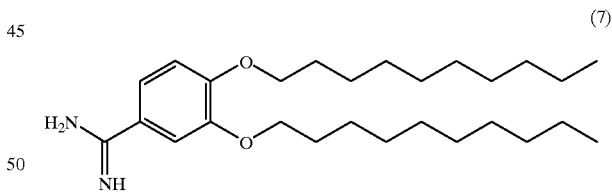

(7)

(EXAMPLE 6)

Liposomes containing the amidine derivatives synthesized in Examples 1 to 5 as a membrane component were prepared in the following manner.

Three μM of an amidine derivative, 21 μM of dipalmitoylphosphatidylcholine (DPPC), and 6 μM of cholesterol were weighed and put into a 10-ml round bottom flask and completely dissolved in 1 ml of chloroform. Chloroform was removed by evaporation with an evaporator under reduced pressure to form a thin lipid film on the inner wall of the flask. One ml of 10 mM Tris-HCl buffer containing 0.5 μM of calcein was added to the flask and stirred by vigorous shaking to obtain a suspension of calcein-entrapping liposomes (MLV).

(Test Example 1) Measurement of Calcein Entrapping Ratio

The ratio of entrapping calcein in liposomes was determined as follows. Forty $\mu$l of a 50-fold diluted liposome suspension was added to 2.0 ml of 10 mM Tris-HCl buffer. Fluorescent intensity of the mixture was measured (exitation wavelength: 490 nm, fluorescent wavelength: 530 nm). The fluorescent intensity measured at this time is referred to as Ft. Twenty $\mu$l of a 10 mM $CoCl_2$ solution was added to the mixture and calcein that was not entrapped into the liposomes was allowed to quench. The fluorescence of calcein entrapped in the liposome was measured. The fluorescent intensity measured at this time is referred to as Fin. Twenty $\mu$l of a 20% Triton X-100 solution was added thereto to destroy the liposomes and bind calcein to $Co^{2+}$ for quenching. The fluorescent intensity measured at this time is referred to as Fq. The retention efficiency of the liposome was calculated by the following equation.

Retention efficiency $(\%) = (Fin - Fq \times r) / (Ft - Fq \times r) \times 100$ In the formula, r is a value by calibrating volume changes of the reaction mixture brought about by adding the liposome suspensions and the drug. In this example, r =(2.0+ 0.04+0.02+0.02)/2.0=1.04. The results are shown in Table 1.

TABLE 1

Ratio of entrapping into liposomes

| Liposome suspension | Entrapping ratio (%) |
|---|---|
| Liposome suspension containing the amidine derivative of Example 1 | 26.77 |
| Liposome suspension containing the amidine derivative of Example 2 | 26.60 |
| Liposome suspension containing the amidine derivative of Example 3 | 27.31 |
| Liposome suspension containing the amidine derivative of Example 4 | 25.75 |
| Liposome suspension containing the amidine derivative of Example 5 | 24.89 |

(EXAMPLE 7)

DNA-entrapping liposomes containing the amidine derivatives synthesized in Examples 1 to 5 as membrane components were prepared in the following manner.

Ten $\mu$M of an amidine derivative, 20 $\mu$M of dilauroylphosphatidylcholine (DLPC), and 20 $\mu$M of dioleoylphosphatidylethanolamine (DOPE) were weighed and dissolved in 1 ml of chloroform to obtain chloroform solution A.

Twenty $\mu$l of the chloroform solution A was put into a 10-ml round bottom flask and 1 ml of chloroform was added. The solvent chloroform was removed with a rotary evaporator to form a lipid thin film on the inner wall of the flask. The film was hydrated by vigorously mixing in 1 ml of steile water containing 20 $\mu$m of plasmid pcDNA/Amp (manufactured by Invitrogen) in which a $\beta$-galactosidase gene was incorporated to produce DNA-entrapping liposomes.

(Test Example 2) Preparation of Cells and Transfection

Cells: Cos-1 cells (ATCC No. CRL-1650) purchased from Dainippon Pharmaceutical Co., Ltd. were subcultured in an Iscove's modified Dulbecco's medium (IMDM) containing 10% fetal calf serum (FCS) in an incubator under 5% $CO_2$ and 95% $O_2$ at 37° C.

Transfection: The Cos-1 cells were cultured after inoculated at a density of about 2 ×$10^4$ cells per each well of a 6-well multi-well plate supplemented with 1 ml of the IMDM containing 10% FCS. After about 24-hour of incubation, the medium was replaced with a fresh medium free from FCS and the liposome suspension containing 0.2 $\mu$g of DNA was added thereto. After 16-hour of transfection, the medium was replaced with a fresh IMDM containing 10% FCS and the cell were further incubated 48 hours. The cells were then fixed with formaldehyde, and then 5-bromo-4-chloro-3-indolyl-$\beta$-galactopyranoside (X-gal) which is a substrate of $\beta$-galactosidase was added to identify the cells that expressed $\beta$-galactosidase. To determine the percentage of transfected cells, the stained cells were image analyzed. The results are shown in Table 2.

TABLE 2

Ratio of incorporated cells

| Samples | Ratio of incorporated cells |
|---|---|
| Liposome containing the amidine derivative of Example 1 | 32.3 ± 3.8 |
| Liposome containing the amidine derivative of Example 2 | 28.3 ± 2.2 |
| Liposome containing the amidine derivative of Example 3 | 20.5 ± 3.8 |
| Liposome containing the amidine derivative of Example 4 | 33.5 ± 4.5 |
| Liposome containing the amidine derivative of Example 5 | 30.0 ± 5.5 |
| Lipofectin (Life Technology) | 5.9 ± 0.91 |
| Gene transfer (Wako Pure Chemical Industries, Ltd.) | 15.0 ± 0.67 |

(EXAMPLE 8)

Rhodamine-labeled liposomes containing the amidine derivative synthesized in Example 1 as a membrane component were prepared in the following manner.

A chloroform solution of lipid consisting of soybean lecithin/cholesterol/amidine derivative (total lipid content: 120 mM, 7/2/1 (molar ratio)) was added to a round bottom flask. The solution was evaporated to dryness with a rotary evaporator under reduced pressure and dried overnight at room temperature under vacuum to form a lipid thin film on the inner wall of the flask. The film was hydrated by vortexing in a vortex mixer at 65° C. in physiological saline (4 ml) to form liposome suspension.

The particle size of the suspension was adjusted by filtering the suspension through a polycarbonate film. An ethanol solution of rhodamine-labeled phosphatidylethanolamine (Avanti) was added to the suspension and allowed to stand at 37° C. for 30 minutes. The mixture was then fully dialyzed against physiological saline using a cellulosic dialysis membrane at 4° C.

(Test Example 3) Accumulation test Using Experimental Nephritis Animal Model.

SD rats (5-week-old, male) was previously bleeded for a week and anti-Thy1.1 antibody (OX7, Serotec) was administered to the caudal vein to induce nephritis. In three to four days after the administration of the antibody, a protein content in urine accumulated for one day was measured to confirm onset of nephritis. The rhodamine-labeled amidine liposomes (the total lipid content of 10 mg/ml of physiological saline) were administered to the caudal vein in a dose of 1 ml/kg. One, six, and twenty-four hours after the administration, the rats were sacrificed by removing blood. Systemic perfusion was performed with heparinized physiological saline, then, liver, spleen, and kidney were excised. Tissue homogenate for each organ was prepared. Rhodamine pigment was extracted from the tissue homogenate with chloroform to determine the concentration of the liposomes in the tissue. The results are shown in Table 3.

As shown in Table 3, the liposomes containing the amidine derivative of the present invention as a membrane component rapidly disappeared in the liver and the spleen of the nephritis induced rats, while the liposomes were outstandingly accumulated in the kidney and the accumulation was continued for 24 hours or longer.

TABLE 3

Dynamics of the amidine liposomes in rats

| Hours after the administration | Accumulation of liposomes (μg lipid/g tissue) | | |
|---|---|---|---|
| | liver | kidney | spleen |
| 1 | 43 | 21 | 75 |
| 6 | 17 | 18 | 20 |
| 24 | 2 | 10 | 1 |

[Acute Toxicity]

Acute toxicity test was performed by orally or intravenously administering the amidine derivatives of the present invention to ICR male mice (5-week-old). As a result, LD$_{50}$ of the amidine derivatives was not less than 320 mg/kg. High safety of the derivatives was confirmed as compared with their effectiveness.

APPLICATION

The present invention provides novel amidine derivatives. The drug carrier such as liposomes or emulsions comprising the amidine derivative of the present invention can enclose genetic materials or drugs and transfer them to cells or affected sites efficiently and safely.

What is claimed is:

1. An amidine derivative represented by the formula (1):

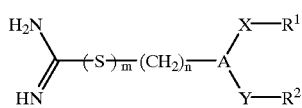

(1)

wherein A is an aromatic ring;

R$^1$ and R$^2$ independently represent an alkyl group or an alkenyl group having 10 to 25 carbon atoms;

X and Y independently the present one member selected from the group consisting of —O—, —S—, —COO—, —OCO—, CONH—, and —HNCO—;

m is 0 or 1; and n is an integer of 0 to 6.

2. The amidine derivative according to claim 1 wherein R$^1$ and R$^2$ are independently an alkyl group having 10 to 18 carbon atoms; X and Y are —O—; R is benzene ring; and m and n are 0.

3. A drug carrier comprising the amidine derivative of claim 1 as its constituent.

4. The drug carrier according to claim 3 wherein said drug carrier is a liposome.

5. The drug carrier according to claim 3 wherein said carrier has encapsulated therein a diagnostic agent or a therapeutic agent.

6. The drug carrier according to claim 5 wherein said agent encapsulated is at least one member selected from the group consisting of a nucleic acid, a polynucleotide and a gene.

7. The drug carrier according to claim 5 wherein said therapeutic agent encapsulated is at least one member selected from the group consisting of an antiinflammatory agent, an anticancer agent, an enzyme inhibitor, an antibiotic, an antiviral agent, an antioxidant.

8. The drug carrier according to claim 5 wherein said agent encapsulated is at least one member selected from the group consisting of a lipid-intake inhibitor, an angiotensinase inhibitor, an angiotensin receptor antagonist, an inhibitor for proliferation and migration of smooth muscle cells, a platelet-aggregation inhibitor, an enhancer or inhibitor of proliferation of vascular endothelial cells, an aldose reductase inhibitor, a mesangial cell-proliferation inhibitor, a lipoxygenase inhibitor, an immunosuppressant, and an immunopotentiator.

9. The drug carrier according to claim 5 wherein said therapeutic agent encapsulated is at least one member selected from the group consisting of an enzyme, a steroid, and a hormone.

10. The drug carrier according to claim 5 wherein said agent encapsulated is a glycosaminoglycan.

11. The drug carrier according to claim 5 wherein said agent encapsulated is a polysaccharide.

12. The drug carrier according to claim 5 wherein said agent encapsulated is a protein or a peptide.

13. The drug carrier according to claim 5 wherein said agent encapsulated is at least one diagnostic agent selected from the group consisting of an X ray contrast medium, an isotope-labeled agent for diagnosis by nuclear medicine, and an agent for diagnosis by nuclear magnetic resonance.

14. A liposome comprising the amidine derivative of claim 1 as its constituent.

15. The liposome according to claim 10 wherein said liposome comprises a hydrophilic polymer selected from the group consisting of polyethylene glycol, dextran, pullulan, Ficoll, polyvinyl alcohol, styrene-maleic anhydride alternating copolymer, divinyl ether-maleic anhydride alternating copolymer, synthetic polyamino acid, amylose, amylopectin, chitosan, mannan, cyclodextrin, pectin. and carrageenan; and a phospholipid selected from the group consisting of phosphatidylglycerol, phosphatidic acid, phosphatidylcholine, phosphatidylethanolamine, phosphatidylserine, phosphatidylinositol, sphingomyelin cardiolipin, and hydrogenated derivatives thereof.

16. The liposome according to claim 10 wherein said liposome further comprises at least one member selected from a stabilizer, an antioxidant or a combination thereof.

17. The liposome according to claim 15 wherein said liposome has an external diameter of 0.02 to 250 μm.

* * * * *